United States Patent [19]

Stennert et al.

[11] Patent Number: 4,899,730
[45] Date of Patent: Feb. 13, 1990

[54] HOLDER FOR MEDICAL INSTRUMENTS

[75] Inventors: Eberhard Stennert, Cologne; Helmut Heckele, Knittlingen, both of Fed. Rep. of Germany

[73] Assignee: Richard Wolf GmbH, Fed. Rep. of Germany

[21] Appl. No.: 281,286

[22] Filed: Dec. 8, 1988

[30] Foreign Application Priority Data

Dec. 11, 1987 [DE] Fed. Rep. of Germany ....... 3742053

[51] Int. Cl.⁴ .............................................. A61B 1/00
[52] U.S. Cl. ...................................... 128/4; 128/897; 224/904
[58] Field of Search ............. 128/4, 20, 303 R, 303 B, 128/897; 224/904

[56] References Cited

U.S. PATENT DOCUMENTS

| | | | |
|---|---|---|---|
| 1,237,121 | 8/1917 | Suffa | 128/20 |
| 1,375,445 | 4/1921 | Crossley | 128/20 |
| 1,398,842 | 11/1921 | Cruse | 128/303 B |

FOREIGN PATENT DOCUMENTS

| | | |
|---|---|---|
| 11160 | 4/1953 | Fed. Rep. of Germany . |
| 1927313 | 11/1965 | Fed. Rep. of Germany . |
| 1245533 | 7/1967 | Fed. Rep. of Germany . |
| 7824396 | 11/1978 | Fed. Rep. of Germany . |

Primary Examiner—William H. Grieb
Attorney, Agent, or Firm—Hill, Van Santen, Steadman & Simpson

[57] ABSTRACT

A holder for medical instruments comprises a holding element fastenable on to the body of a patient, for example in the form of a strap or a hoop, on which is fixedly mounted at least one rigid rail which carries mountings for endoscopes and/or auxiliary instruments. The instrument mountings are adjustably secured to the rail by means of couplings. The instruments can thus be mounted so as to be pivotable relative to the rail and/or displaceable along it.

19 Claims, 1 Drawing Sheet

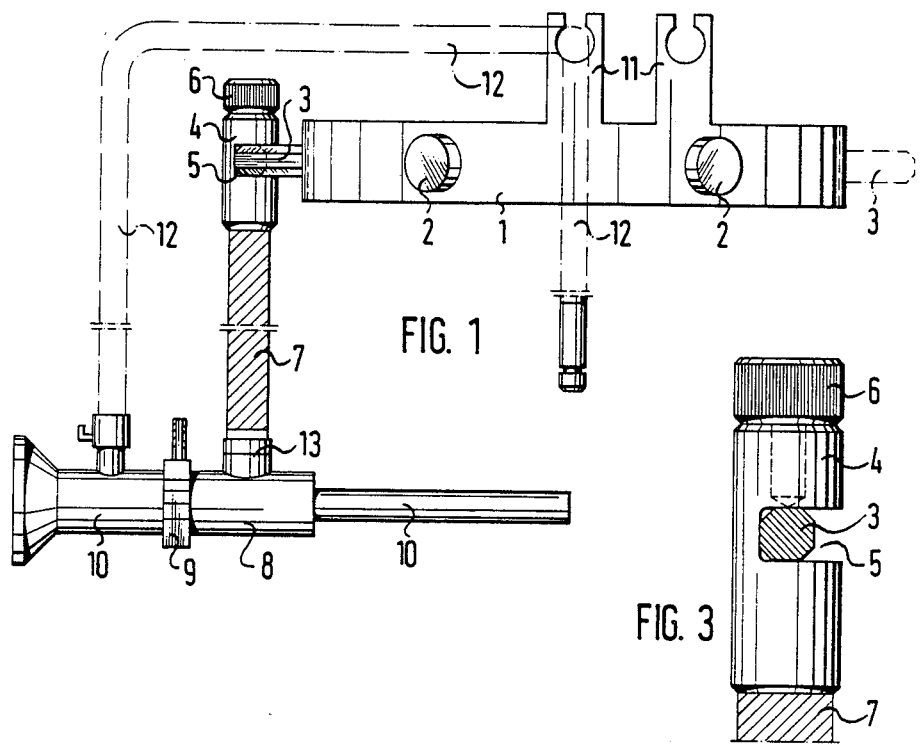
FIG. 1
FIG. 3
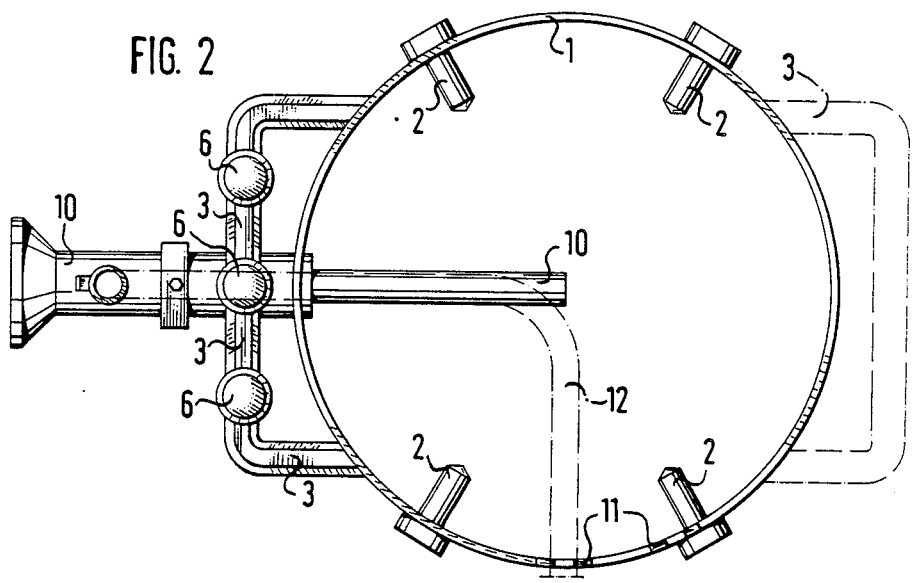
FIG. 2

HOLDER FOR MEDICAL INSTRUMENTS

BACKGROUND OF THE INVENTION

1. Field of the Invention

This invention relates to a holder for medical instruments, and in particular to a holder of the type comprising a support element attachable to a part of a patient's body, on which is secured a carrier for fixedly clampable instruments such as an endoscope.

2. Description of the Prior Art

German Utility Model Specification 7824396 discloses an instrument holder of the aforementioned type in which the support element comprises a head strap with a balljoint mounting and a clamping device for an endoscope, which may optionally be set in front of the left or right eye of the physician, without the position of the endoscope having to be retained.

SUMMARY OF THE INVENTION

It is an object of the present invention to provide an instrument holder of the aforementioned with its support constructed in such a way that a plurality of medical instruments may be connected thereto and immobilised with respect to the point of therapy, and wherein accidental changes in position caused by unintentional movements are prevented.

This object is achieved in accordance with the invention in that an instrument holder of the aforementioned type has a support element which has fixedly secured thereto at least one rigid rail with couplings thereon by means of which endoscopes, auxiliary instruments and the like can be adjustably secured to the rail.

Further objects and advantages of the invention will become apparent from the following detailed description, read in conjunction with the accompanying drawings which illustrate a preferred embodiment of the invention.

BRIEF DESCRIPTION OF THE DRAWINGS

In the drawings:

FIG. 1 shows a sideview of an instrument holder in accordance with the invention with an endoscope fitted;

FIG. 2 shows a plan view of the holder of FIG. 1 and

FIG. 3 shows a sideview of a coupling element on a rail in an enlarged detail of the holder of FIG. 1.

DETAILED DESCRIPTION OF THE PREFERRED EMBODIMENT

The instrument holder comprises a band-shaped support element 1, for example in the form of a strap or hoop. This element may for example be laid around the head, the thigh or another part of the body of a patient and secured for example by means of radially adjustable peripherally distributed screws 2. The screws 2 may be provided with surface-bearing contact means where the holder is to be secured to a thigh or other soft part of the body.

The support element 1 is firmly secured to at least one rigid rail 3 on which is mounted a plurality of couplings 4. These couplings 4 have an incision 5 at one side to receive the rail 3, so that the required number of couplings 4 may be installed in a simple manner on rail 3, which is of non-circular cross-section, on pivoted to the desired annular position relative to the rail and immobilised by means of a screw 6. Instead of the screw 6, spring-loaded detent balls or catches may be provided.

Each coupling 4 is provided with an intermediate member 7 which is advantageously made partially flexible or with an articulation, so that an instrument mounting 8 adjustably connected thereto may be moved to any desired position. In the case of FIG. 1, the mounting 8 is so constructed that an endoscope 10 passed through it and is secured to the mounts of by means of a clamping ring 9. To this end, the intermediate member 7 may be connected to the mounting 8 at 13 by means of a screw joint or any other suitable connection. The mounting 8 is appropriately constructed to correspond to other auxiliary instruments or devices.

The support element 1, which may suitably be constructed as a metal strap, is provided furthermore with carriers 11 which advantageously are received on the holding element in a looped manner and are displaceable along the element. These carriers serve the purpose of supporting elongate flexible supply means 12 such as hoses, cables and light guides and of adjusting these to an advantageous position These carriers may also be secured rigidly on the holding strap or, as shown in FIG. 1, be formed integrally with the support element.

If the support element for medical instruments is produced in the form of a resilient helical coil, the fastening devices 2 may be omitted. The immobilisation on the circumference of a body member is then performed by initially expanding the coil against its spring force, manoeuvering it over the body member in question and thereafter releasing the spring whereby the coil is immobilised on the surface of the body.

In another embodiment of the holder according to the invention, it may be envisaged to replace the holding strap by a hoop, to which end the rail 3 for attachment of the coupling 4 will be integrated in the circumference of the hoop and have a matching configuration.

As an alternative, a holding strap, for example of metal or rigid plastics material, could extend around less than the whole circumference of the body member and have, its free ends connected together by a stretchable connection such as an elasticated strap or a pair of such straps with a buckle or other connection between them.

What is claimed is:

1. A holder for medical instruments, comprising: a support element having means for securing it to a part or a patient's body;
    at least one elongated rigid rail secured to said support element; coupling means mounted on said rigid rail; and at least one mounting for a medical instrument being adjustably secured to said coupling means.

2. A holder as claimed in claim 1, wherein said coupling means are releasably secured to said rail.

3. A holder as claimed in claim 1 wherein coupling means are longitudinally displaceable on said rail.

4. A holder as claimed in claim 1, wherein said means for securing comprises radially displaceable fastening devices distributed peripherally around the support element to secure said support element to a patient's body.

5. A holder as claimed in claim 1 further comprising at
    one carrier on said support element to carry elongate flexible supply means for an instrument mounted on said holder.

6. A holder as claimed in claim 5 wherein at least one carrier is displaceably mounted on said support element.

7. A holder as claimed in claim 5 wherein at least one carrier is formed integrally with said support element.

8. A holder as claimed in claim 1 wherein said support element is in the form of a strap.

9. A holder as claimed in claim 1 wherein said support element is in the form of a hoop, said rail being of matching configuration and being integrally formed thereon.

10. A holder as claimed in claim 1 wherein said support element is in the form of a helical coil.

11. A holder as claimed in claim 1 wherein said support element is constructed as a band directly mountable on a body member, said band having two free ends aligned with one another with a stretchable connection between the free ends.

12. A holder for medical instruments comprising: a support element having means for securing the element to a part of a patient's body; at least one rigid rail being secured to said support element; coupling means having means for releasably mounting the coupling means in any position on said rail, each coupling means having an intermediate member capable of pivotable displacement; a mounting for a medical instrument being adjustable secured to each intermediate member; and at least one carrier being provided on the support element to carry elongated flexible supply means for an instrument mounted in one of said mountings.

13. A holder according to claim 1, comprising said holder having a plurality of said mountings and coupling means, each coupling means including a coupling and an intermediate member, each intermediate member adjustably connecting the mounting to said coupling and each coupling being pivotally displaceable and being immobilizable relative to the rigid rail.

14. A holder as claimed in claim 13, wherein said intermediate member is angularly deflectable and comprises at least two elements which are pivotally deflectable in an articulated manner.

15. A holder as claimed in claim 13 wherein said intermediate member is partially flexibly constructed so as to be angularly deflectable.

16. A holder for medical instruments comprising:
a support element having means for securing the support element to a part of a patient's body; at least one elongated rigid rail being secured to said support element and having a non-circular cross-section; coupling means being mounted on said rigid rail; and a mounting for medical instruments being adjustably secured to said coupling means.

17. A holder according to claim 16 which includes a carrier on said support element to carry elongate flexible supply means for an instrument mounted on said holder.

18. A holder according to claim 16, wherein said coupling means includes a coupling pivotally displaceable and immobiligable relative to said rigid rail and an intermediate member connected to said coupling, said intermediate member being adjustably to adjustably connect the mounting to said coupling.

19. A holder according to claim 16 wherein said coupling means is reasonably secured on said rail and is displaceable therealong to enable adjusting the position on said elongated rail.

* * * * *